United States Patent [19]

Pedersen

[11] 4,171,316

[45] Oct. 16, 1979

[54] PREPARATION OF MALEIC ANHYDRIDE USING A CRYSTALLINE VANADIUM(IV)BIS(METAPHOSPHATE) CATALYST

[75] Inventor: S. Erik Pedersen, Havertown, Pa.

[73] Assignee: Atlantic Richfield Company, Los Angeles, Calif.

[21] Appl. No.: 889,785

[22] Filed: Mar. 24, 1978

[51] Int. Cl.$^2$ .......................................... C07D 307/60
[52] U.S. Cl. ................................ 260/346.75; 252/437
[58] Field of Search ................................... 260/346.75

[56] References Cited

U.S. PATENT DOCUMENTS 3,255,211  6/1966  Kerr ................................ 260/346.75

OTHER PUBLICATIONS

Nakamura et al., Journal of Catalysis 34, pp. 345-355 (1974).
Tofield et al., Journal of Chemical Society-Dalton Transactions, (1975), pp. 1806-1810.

*Primary Examiner*—John M. Ford
*Assistant Examiner*—Bernard Dentz
*Attorney, Agent, or Firm*—Delbert E. McCaslin

[57] ABSTRACT

A process for the preparation of maleic anhydride in high yield and selectivity which comprises partially oxidizing an unsaturated aliphatic hydrocarbon selected from 1-butene, 2-butene and 1,3-butadiene or mixtures thereof in the vapor phase at elevated temperatures with oxygen or an oxygen-containing gas in the presence of a single phase vanadium(IV)bis(metaphosphate) catalyst having the formula $VO(PO_3)_2$. Preferably the reaction is carried out in the presence of steam to enhance the selectivity to maleic anhydride.

10 Claims, No Drawings

PREPARATION OF MALEIC ANHYDRIDE USING A CRYSTALLINE VANADIUM(IV)BIS(METAPHOSPHATE) CATALYST

FIELD OF THE INVENTION

The present invention relates to a process for preparing maleic anhydride from certain unsaturated aliphatic hydrocarbons by contacting a feed of said hydrocarbons and an oxygen-containing gas with a single phase vanadium(IV)bis(metaphosphate) catalyst.

BACKGROUND OF THE INVENTION

A number of prior art processes have been proposed for the preparation of dicarboxylic anhydrides, such as maleic anhydride, by the catalytic oxidation of certain hydrocarbons such as the n-butenes, 1,3-butadiene, benzene and n-butane in the presence of air or other oxygen-containing gases at elevated temperatures using phosphorus-vanadium-oxygen catalyst systems which systems generally include other metals or metal compounds as potential yield improving co-catalysts such as molybdenum, copper and uranium oxides or other oxides incorporated into the catalyst system during preparation. Such catalysts are generally not well defined and usually comprise a number of compounds or phases, any one of which may act as the actual oxidation catalyst. These catalyst systems however, as well as other catalysts showing some activity for the production of maleic anhydride have generally proven to be unsatisfactory for commercial application and leave a lot to be desired since the yield of and selectivity to maleic anhydride is usually low. For example, a catalyst system for the preparation of maleic anhydride comprising vanadium pentoxide and oxides of phosphorus and molybdenum as described in Japanese Pat. No. 12,327/1972 to Yokayama et al only gave a yield of 48 percent.

The typical phosphorus-vanadium-oxygen catalyst system is usually prepared by reducing vanadium pentoxide to vanadium (IV) in water or an organic solvent with hydrochloric acid or other suitable reducing agents. A source of phosphorus, usually phosphoric acid, is mixed with the vanadium (IV) solution to produce a catalyst precursor which is heat treated to give the production catalyst. Co-catalysts as above described, for example, are usually incorporated into the catalyst system during the solution stage of preparation.

U.S. Pat. No. 4,062,873 and the numerous patent references noted therein, all of which are deemed to be reiterated herein, describe various vanadium-phosphorus oxide catalyst systems employed in producing maleic anhydride from n-butane and particularly the n-butenes.

U.S. Pat. No. 3,907,835 discloses a gas phase process for the production of maleic anhydride by the catalytic oxidation of an unsaturated hydrocarbon as well as an aldehyde with a gas containing free molecular oxygen under oxidation conditions in the presence of a catalyst of an admixture of vanadium, uranium, phosphorus and oxygen.

One process which has been commercialized is shown in U.S. Pat. No. 3,904,652 which discloses a process for the oxidation of n-butane to form maleic anhydride over a phosphorus-vanadium-oxygen complex catalyst containing one or more metal activators selected from zinc, copper, bismuth or lithium and maintaining a particular concentration of the n-butane in the reaction zone.

U.S. Pat. No. 3,864,280 describes a crystalline phosphorus-vanadium mixed oxide hydrocarbon oxidation catalyst composition consisting primarily of pentavalent phosphorus, vanadium and oxygen, useful for the production of acid anhydrides such as maleic anhydride.

U.S. Pat. No. 3,366,648 discloses a process for the production of maleic anhydride by contacting butene-1, butene-2, butadiene-1,3 or mixtures thereof in the vapor phase at elevated temperatures with oxygen and a vanadium-phosphorus catalyst complex having an atomic ratio of from about 1.0:2.0 atoms of phosphorus per atom of vanadium and as a phosphorus stabilizer an element of Group IA of the Periodic Table.

U.S. Pat. No. 3,293,268 discloses a method for the preparation of maleic anhydride which comprises oxidizing n-butane in the presence of a phosphorus-vanadium-oxygen-containing complex catalyst prepared by reacting phosphoric acid with vanadium oxalate in aqueous solution, by reacting phosphoric acid with ammonium metavanadate in aqueous solution or by reacting a phosphorus compound selected from phosphoric acid and $P_2O_5$ with a vanadium compound in an aqueous solution of a hydrogen halide, to give a catalyst having particular gram atoms of phosphorus per gram atom of vanadium.

SUMMARY OF THE INVENTION

According to the present invention there is provided an improved process for producing maleic anhydride which process comprises oxidizing an unsaturated aliphatic hydrocarbon selected from 1-butene, 2-butene and 1,3-butadiene or mixtures thereof at a temperature in the range of from about 300° C. to 600° C. by contacting said hydrocarbon and oxygen or an oxygen-containing gas with a catalyst comprising the single phase compound vanadium(IV)bis(metaphosphate) at contact times of from about 0.5 to 10 seconds of reactant feed over the catalyst.

The instant process employing the single phase vanadium(IV)bis(metaphosphate) catalyst provides much improved yields of maleic anhydride, which catalyst compound is easily prepared and characterized as compared to the typical vanadium-phosphorus-oxygen catalysts exemplified by the prior art processes.

It is a primary object of this invention to provide a process for the preparation of maleic anhydride in high yield and high conversion of reactants by the catalytic oxidation of unsaturated aliphatic hydrocarbons such as 1-butene, 2-butene or 1,3-butadiene or mixtures thereof.

It is another object of this invention to provide such a process employing a novel type single phase vanadium(IV)bis(metaphosphate) catalyst, which provides yields of and selectivities to maleic anhydride which are higher than heretofore obtained by the oxidation of unsaturated aliphatic hydrocarbons.

These and other objects and advantages of this invention will become apparent from the description of the invention which follows and from the claims.

DESCRIPTION OF THE INVENTION

In accordance with the invention, maleic anhydride is produced by oxidizing 1-butene, 2-butene or 1,3-butadiene or mixtures thereof under controlled temperature conditions of from about 300° C. to 600° C. in the presence of a high performance single phase vanadium(IV)bis(metaphosphate) compound, $VO(PO_3)_2$.

The VO(PO$_3$)$_2$ compound, with some of its properties, which is employed in the present invention as catalyst, is disclosed and may be prepared according to a method set forth in an article by Bruce C. Tofield, et al, *Journal of the Chemical Society, Dalton Transactions*, Part II, 1975, pp. 1806–1810 as well as G. Ladwig, Z. Chem., 1968, Vol. 8, p. 307 referred to therein which articles are incorporated herein by reference. The catalyst possesses a vanadium oxygen double bond and high a highly ordered structure.

After preparation the VO(PO$_3$)$_2$ compound is generally dried at 120° C., calcined in air at 450° C. for at least two hours then broken up and sieved to the appropriate Tyler Standard Sieve mesh size, usually for fixed bed reactor use. The resulting VO(PO$_3$)$_2$ compound (catalyst precursor) which has a surface area of approximately 0.30 to 0.50 m$^2$/gm. requires a period of activation of conditioning for use in oxidizing the above indicated unsaturated aliphatic hydrocarbons. For the activation or conditioning the catalyst precursor is subjected to temperatures which are at or above the oxidation reaction temperatures of from about 300° C. to 600° C. preferably from 450° C. to 550° C., under a flow of from about 0.2 volume percent to about 2.0 volume percent preferably 0.5 to 1.5 in air of said hydrocarbon or mixture of hydrocarbons to be oxidized, at an apparent contact time of from about 1 to 10 seconds, preferably 4 to 8 seconds for an appropriate period, with subsequent temperature and flow rate adjustments to desired reaction conditions, to enable the hydrocarbon conversion to reach 90 percent or more. The length of time required for activation or conditioning of the catalyst precursor and to permit the catalyst performance to become stabilized depends on the temperature employed and contact time of the hydrocarbon-air mixture but generally will be from about 4 to 8 hours. Apparent contact time calculated in seconds is equal to the flow rate of the hydrocarbon-air feed mixture at cc/seconds, per cc of catalyst measured at ambient conditions. Once activated the VO(PO$_3$)$_2$ exhibits excellent performance as a catalyst for the oxidation of 1-butene, 2-butene and 1,3-butadiene or mixtures thereof to maleic anhydride for extended periods of time.

Oxygen-containing gas such air or oxygen diluted with an inert gas such as nitrogen, helium, etc., is generally employed in the process although purified oxygen can also be used. Usually and preferably, air will be employed, along with the unsaturated hydrocarbon, as the oxidizing gas. Under the high temperature conditions of this reaction, mixtures of the unsaturated hydrocarbons employed and air form an explosive mixture. To avoid such conditions, the concentration of the unsaturated hydrocarbons in the feed gas stream generally a hydrocarbon in air mixture, to the reactor is suitably maintained at from 0.2 to 2.0 volume percent and preferably 1.0 to 1.5 volume percent to obtain essentially the optimum yield of product for the process. Higher percentage concentrations of the hydrocarbon in the feed gas stream may be employed above the explosive range.

The oxidation reaction may be carried out with a variety of reactors. For example, multiple tube heat exchange type reactors have been found to be satisfactory. In the laboratory the reaction was carried out using a ⅜ inch I.D. stainless steel U-tube reactor immersed in a fluidized sand bath heat transfer system to maintain a steady temperature. The immersed lower portion of the U-tube was filled with 8 to 16 mesh catalyst granules over which a hydrocarbon-air feed was passed, usually with steam.

The oxidation reaction is an exothermic reaction and therefore, methods must be employed to control the reaction temperature to prevent overheating in portions of the catalyst bed and total oxidation of the hydrocarbons to by-products such as CO$_2$. Any suitable cooling means may be employed to aid temperature control. Such media may include various sand, chemical or salt baths which may be kept at the proper temperature by heat exchangers and the like to conduct heat away from the walls of the reactor and control the reaction.

The reaction will proceed at temperatures of from about 300° C. to 600° C. It is generally preferred to operate the process at temperatures in the range of from 400° C. to 500° C. to obtain a convenient rate of reaction and conversion of the unsaturated hydrocarbon to maleic anhydride. The reaction pressures for the present invention are generally atmospheric but pressures of up to about 1000 psig may be employed. Pressures between 10 and 100 psig are preferred. Subatmospheric pressures may also be utilized but have no added advantage in the process. The feed mixture of the unsaturated hydrocarbon or mixture of hydrocarbons and oxygen-containing gas, such as air, is contacted with the catalyst of this invention at the desired reaction temperature and apparent contact times over the catalyst of from about 0.5 to 10 seconds and preferably from 1.5 to 4 seconds.

It has also been determined that the yield of maleic anhydride is substantially increased, in the order of 10 percent or better, when steam is added to the reactant feed stream. Thus, steam may constitute up to about 50 volume percent and preferably between 2 and 20 volume percent of said feed stream during reaction. With steam addition to the reactant feed employing the VO(PO$_3$)$_2$ catalyst, maleic anhydride selectivities of between 62 and 66 mole percent with hydrocarbon conversions in the mid to high nineties are obtained for extended periods of time.

Although the VO(PO$_3$)$_2$ catalyst of this invention may be prepared in the approriate mesh size and employed in the reactor as such, it may also be on inert support materials or carriers such as silica gel, alumina, silicon carbide, aluminosilicates and kieselguhr. The catalyst support, if employed, provides a surface for the catalyst and gives physical strength and stability to the catalyst material.

The maleic anhydride produced by the present process may be recovered in a number of ways well known to those skilled in the art. For example, solid maleic anhydride may be collected directly by suitable non-aqueous cooling of the effluent products and separation of the solid maleic anhydride from any unreacted unsaturated hydrocarbon and inert gases. The recovery may be by direct condensation or by adsorption in a suitable media with subsequent separation and purification of product. The gaseous effluent from the reactor may also be passed through or quenched with water which converts the maleic anhydride to maleic acid which may be suitably separated and recovered for example by evaporation and converted back to maleic anhydride by well known dehydration methods.

The following examples are provided to illustrate the invention in accordance with the principles of this invention but are not to be construed as limiting the invention in any way except as indicated by the appended claims.

In the Examples which follow the oxidation reactions were run in a ⅜ inch inside diameter stainless steel U-tube reactor which was immersed in a fluidized sand bath for maintaining the temperature of reaction. The lower half of the U-tube reactor was filled with catalyst having an 8–16 mesh (Standard Sieve). The (precursor) catalyst is activated or conditioned in a stream of air with 1 volume percent of unsaturated hydrocarbon at a desired temperature for several hours at a desired apparent contact time over the catalyst. Following activation, the temperature is decreased to the desired oxidation reaction temperature and the flow of hydrocarbon-air mixture, with or without the addition of steam, adjusted to the desired apparent contact time of between about 2.0 and 4.0 seconds. The gaseous effluent oxidation reaction products from the reactor were passed through a series of water traps to absorb the maleic anhydride and other by-products such as trace amounts of acetic and acrylic acids; the maleic anhydride being converted to maleic acid in the aqueous solution. The gaseous effluent from the U-tube reactor was analyzed by InfraRed (I.R.) and gas chromatography to determine the concentration of carbon dioxide, carbon monoxide and any unconverted hydrocarbon. The aqueous solution containing the maleic acid was analyzed by gas chromatography and titrated to give the acid number to determine maleic anhydride yield and selectivity. Percent conversion of hydrocarbon and percent selectivity to maleic anhydride are calculated in mole percent.

EXAMPLE 1

A $VO(PO_3)_2$ catalyst for the oxidation of 1-butene, 2-butene and 1,3-butadiene to maleic anhydride was prepared as follows: 15 g. of vanadium pentoxide ($V_2O_5$), and 150 ml. of 85 percent phosphoric acid was mixed in a vitreous graphite crucible. The mixture was heated slowly with a heating mantle to approximately 300° C. with no significant reduction of the vanadium occurring. On further heating of the mixture to between 350° C.–400° C. for 60–90 minutes reduction to vanadium (IV) occurred with the evolution of oxygen. When the evolution of oxygen ceased, the hot solution was quenched with water from which blue crystals of the compound vanadium(IV)bis(metaphosphate), $VO(PO_3)_2$, having a surface area of approximately 0.30 $m^2/gm$. was recovered, dried at 120° C. and calcined in air at 450° C. for two hours. After calcination the vanadium(IV)bis(metaphosphate) was broken up (8–16 mesh) and loaded into the U-tube reactor. X-ray analysis (powder diffraction patterns) of the freshly prepared and activated $VO(PO_3)_2$ catalyst, as well as catalyst which had been on stream for a period of 325 hours in the presence of 5–14 percent steam were identical. The $VO(PO_3)_2$ is insoluble in all conventional solvents and cannot be oxidized at temperatures as high as 1000° C. in air.

EXAMPLE 2

50 ml. of vanadium(IV)bis(metaphosphate) of Example 1 was loaded into the lower half of the U-tube reactor which was immersed in a fluidized sand bath. The catalyst (precursor) was activated in a stream of air and 1 volume percent of 2-butene at 520° C. for two hours at an apparent contact time of 7.2 seconds during which period the activity of the catalyst gradually increased to approximately 100 percent conversion of the 2-butene. Following activation or conditioning of the catalyst, the reaction temperature was decreased to 460° C. and the apparent contact time adjusted to 2.4 seconds for the 2-butene-air reactant feed. In a similar manner without reactivating the catalyst, 1-butene and 1,3-butadiene were oxidized over the same catalyst under slightly varying conditions. No steam was added to the reaction system. Results giving conversions and selectivities are tabulated in Table 1 below.

TABLE 1

| Run No. | Time (hours) | Hydrocarbon | Contact Time (sec.) | Temp. °C. | Mole[1] % Conversion | Mole % Selectivity[2] to M.A. |
|---|---|---|---|---|---|---|
| 1 | 4 | 2-butene | 2.4 | 460 | 97 | 58 |
| 2 | 4 | 1-butene | 2.2 | 460 | 98 | 58 |
| 3 | 4 | 1,3-butadiene | 2.0 | 450 | 99 | 59 |
| 4 | 2 | 2-butene | 2.5 | 480 | 99 | 59 |

[1]% Conversion of hydrocarbon analyzed by gas chromatograph and I.R.
[2]% Selectivity to maleic anhydride (M.A.) by gas chromatograph analysis and titation to give the acid number.

EXAMPLE 3

A number of runs were made employing 50 ml of the catalyst of Example 1 with 1.5 percent 2-butene in air, which catalyst was activated as in Example 2, with the exception that steam was added to the reactant feed stream after adjustment to desired reaction temperatures and apparent contact times for the feed stream. Conditions, selectivities and conversions are tabulated in Table 2 below.

TABLE 2

| Run No. | Time (hours) | Steam Vol. % | Temp. °C. | Contact Time (sec.) | Mole % Conversion | Mole % Selectivity to M.A. |
|---|---|---|---|---|---|---|
| 1 | 7 | 5 | 480 | 2.8 | 97 | 65.0 |
| 2 | 10 | 7 | 460 | 2.4 | 97 | 64.2 |
| 3 | 15 | 8 | 470 | 3.0 | 98 | 64.8 |

EXAMPLE 4

A number of runs were made using 50 ml of the vanadium(IV)bis(metaphosphate) of Example 1. The catalyst (precursor) was loaded into the U-tube reactor and immersed in a fluidized sand bath for temperature control. The catalyst was activated in a stream of air with 1 volume percent 1-butene at 550° C. for 3 hours at an apparent contact time of 7.0 seconds. Following activation the reaction temperature and apparent contact time was adjusted to desired conditions for the various runs and steam was added to the 1 percent 1-butene in air reactant feed stream. The results including conditions are shown in Table 3.

TABLE 3

| Run No. | Time (hours) | Steam Vol. % | Temp °C. | Contact Time (sec.) | Mole % Conversion | Mole % Selectivity to M.A. |
|---|---|---|---|---|---|---|
| 1 | 7 | 8 | 480 | 3.5 | 98 | 65.2 |
| 2 | 15 | 7 | 480 | 3.2 | 97 | 65.0 |
| 3 | 7 | 5 | 470 | 2.8 | 97.5 | 64.6 |
| 4 | 7 | 7 | 460 | 3.5 | 97 | 65.6 |
| 5 | 15 | 5 | 480 | 2.8 | 98 | 64.3 |

EXAMPLE 5

Runs were made with 1,3-butadiene using 50 ml. of the vanadium(IV)bis(metaphosphate) of Example 1. The catalyst was activated in a stream of air with 1 volume percent 1,3-butadiene at 500° C. for 2.5 hours at an apparent contact time of 7.2 seconds. When the activity increased to approximately 100 percent conversion of the 1,3-butadiene, the reaction temperature and apparent contact time was adjusted to desired conditions and steam was added to the 1 percent 1,3-butadiene-air reactant feed stream. The results are shown in Table 4 below.

TABLE 4

| Run No. | Time (hours) | Steam Vol. % | Temp. °C. | Contact Time (sec.) | Mole % Conversion | Mole % Selectivity to M.A. |
|---|---|---|---|---|---|---|
| 1 | 7 | 8 | 450 | 3.0 | 99 | 66.1 |
| 2 | 15 | 5 | 460 | 3.2 | 98 | 65.6 |
| 3 | 10 | 12 | 460 | 3.4 | 98 | 65.2 |
| 4 | 6 | 14 | 465 | 3.8 | 98 | 65.4 |
| 5 | 23 | 3 | 460 | 3.5 | 97 | 65.7 |

EXAMPLE 6

Example 5 was repeated using the same catalyst but with a 1 percent mixture of a $C_4$ fraction of hydrocarbons in air with steam added to the reactant feed. The n-butane contained in the mixture was relatively inert at reaction temperatures; not converting to maleic anhydride to any degree. The contained isobutylene at the process conditions was essentially totally decomposed to $CO_2$, CO and water. Results are shown in Table 5 below.

TABLE 5

| Run No. | Time (hours) | Steam Vol. % | Temp. °C. | Contact Time (sec.) | Mole % Conversion | Mole % Selectivity to M.A. |
|---|---|---|---|---|---|---|
| 1$^{(a)}$ | 5 | 8 | 460 | 3.0 | 99 | 65.2 |
| 2$^{(b)}$ | 5 | 6 | 470 | 3.5 | 98 | 64.8 |

$^{(a)}C_4$ fraction - 51 per cent 1,3-butadiene, 31 per cent n-butenes, 10 per cent isobutylene, 8 per cent n-butane.
$^{(b)}C_4$ fraction - 40 per cent 1,3-butadiene, 39 per cent n-butenes, 14 per cent isobutylene, 7 per cent n-butane.
$^{(c)}$Mole % Conversion of unsaturated hydrocarbons.

I claim:
1. A process for the preparation of maleic anhydride which comprises oxidizing an unsaturated aliphatic hydrocarbon selected from the group consisting of 1-butene, 2-butene and 1,3-butadiene or mixtures thereof in the vapor phase at temperatures in the range of about 300° C. to 600° C. and pressure of from about ambient pressures to 1000 psig with oxygen or an oxygen containing gas in the presence of a single phase crystalline vanadium(IV)bis(metaphosphate) catalyst having a surface area of from about 0.30 to 0.50 m²/g.

2. A process according to claim 1 wherein the unsaturated hydrocarbon is n-butene.

3. A process according to claim 1 wherein the reaction is carried out in the presence of up to 50 volume percent steam added to the reactant feed stream.

4. A process according to claim 3 wherein from about 2 to 20 volume percent steam is added to the reactant feed stream.

5. A process according to claim 1 wherein the temperature is in the range of about 400° C. to 500° C.

6. A process according to claim 1 wherein the oxygen-containing gas is air.

7. A process for the preparation of maleic anhydride which comprises contacting a gaseous feed stream of from about 0.2 to 2 percent n-butene in air and from about 2 to 20 volume percent steam at a temperature of 400° C. to 500° C. with an activated single phase crystalline vanadium(IV)bis(metaphosphate) catalyst having a surface area of from about 0.30 to 0.50 m²/g. at an apparent contact time over the catalyst of from 0.5 to 10 seconds.

8. A process according to claim 7 wherein the feed stream contains from about 1 to 1.5 percent n-butene in air and the contact time over the catalyst is from 1.5 to 4 seconds.

9. A process for the preparation of maleic anhydride which comprises contacting a gaseous feed stream of from about 0.2 to 2 percent 1,3-butadiene in air and from about 2 to 20 volume percent steam at a temperature of 400° C. to 500° C. with an activated single phase crystalline vanadium(IV)bis(metaphosphate) catalyst having a surface area of from about 0.30 to 0.50 m²/g. at an apparent contact time over the catalyst of from 0.5 to 10 seconds.

10. A process according to claim 9 wherein the feed stream contains from about 1 to 1.5 percent n-butene in air and the contact time over the catalyst is from 1.5 to 4 seconds.

* * * * *